United States Patent [19]

Spector et al.

[11] Patent Number: 4,731,521

[45] Date of Patent: Mar. 15, 1988

[54] ELECTRIC CIGAR LIGHTER HAVING AROMATIC EMITTING MEANS

[75] Inventors: Donald Spector, Union City, N.J.; Melvin Spat, Stamford; Dominic Pesapane, West Haven, both of Conn.; Craig M. Saunders, Sagamore Hills, Ohio

[73] Assignees: Casco Products Corporation, Bridgeport, Conn.; Scentronic Industries, Inc., New York City, N.Y.

[21] Appl. No.: 37,044

[22] Filed: Apr. 10, 1987

[51] Int. Cl.$^4$ .............................................. A61L 9/03
[52] U.S. Cl. .................................. 219/274; 219/275; 219/260
[58] Field of Search ............... 219/271, 272, 273, 274, 219/275, 276, 260, 262, 265, 267, 270, 263, 264; 422/305, 306, 125

[56] References Cited

U.S. PATENT DOCUMENTS

| | | | |
|---|---|---|---|
| 1,561,814 | 11/1925 | Aske | 219/274 |
| 1,850,076 | 3/1932 | Hacker | 219/275 |
| 2,010,675 | 8/1935 | Lewis | 219/261 |
| 2,599,485 | 6/1952 | Robinson | 219/275 |
| 2,701,836 | 2/1955 | Pavenick | 219/262 |
| 2,733,333 | 1/1956 | Peters | 219/272 |
| 2,898,649 | 8/1959 | Murray | 422/125 |
| 3,006,042 | 10/1961 | Calandra | 219/276 |
| 3,288,556 | 11/1966 | Weber, III | 422/125 |
| 3,551,092 | 12/1970 | Masson | 219/276 |
| 3,870,857 | 3/1975 | Horwitt et al. | 219/267 |
| 4,574,181 | 3/1986 | Spector | 219/274 |

FOREIGN PATENT DOCUMENTS

| | | | |
|---|---|---|---|
| 1322977 | 2/1963 | France . | |
| 55-23853 | 8/1978 | Japan | 219/274 |
| 2062199 | 5/1981 | United Kingdom | 219/274 |

OTHER PUBLICATIONS

Single Page, Description of Scentron Auto Fragrancer/Lighter, on Sale in U.S.A. more than 1 Year Prior to Filing Date of Present Application.

Primary Examiner—E. A. Goldberg
Assistant Examiner—Teresa J. Walberg
Attorney, Agent, or Firm—H. Gibner Lehmann; K. Gibner Lehmann

[57] ABSTRACT

A scent-emitting electric cigar lighter having an igniting unit with a plug body containing an electric heating element at its inner end, a metal conductor stud connected to the heating element in heat-exchanging relation therewith and extending forwardly through the plug body, and a heat transfer flange at the forward end of the stud. A slab of scent-emitting material, adapted to release aromas in response to heating, is carried in a removable cartridge which is disposed adjacent the heat-transfer flange. Mounted at the front of the plug body is a knob which receives the cartridge and scent-emitting slab.

25 Claims, 15 Drawing Figures

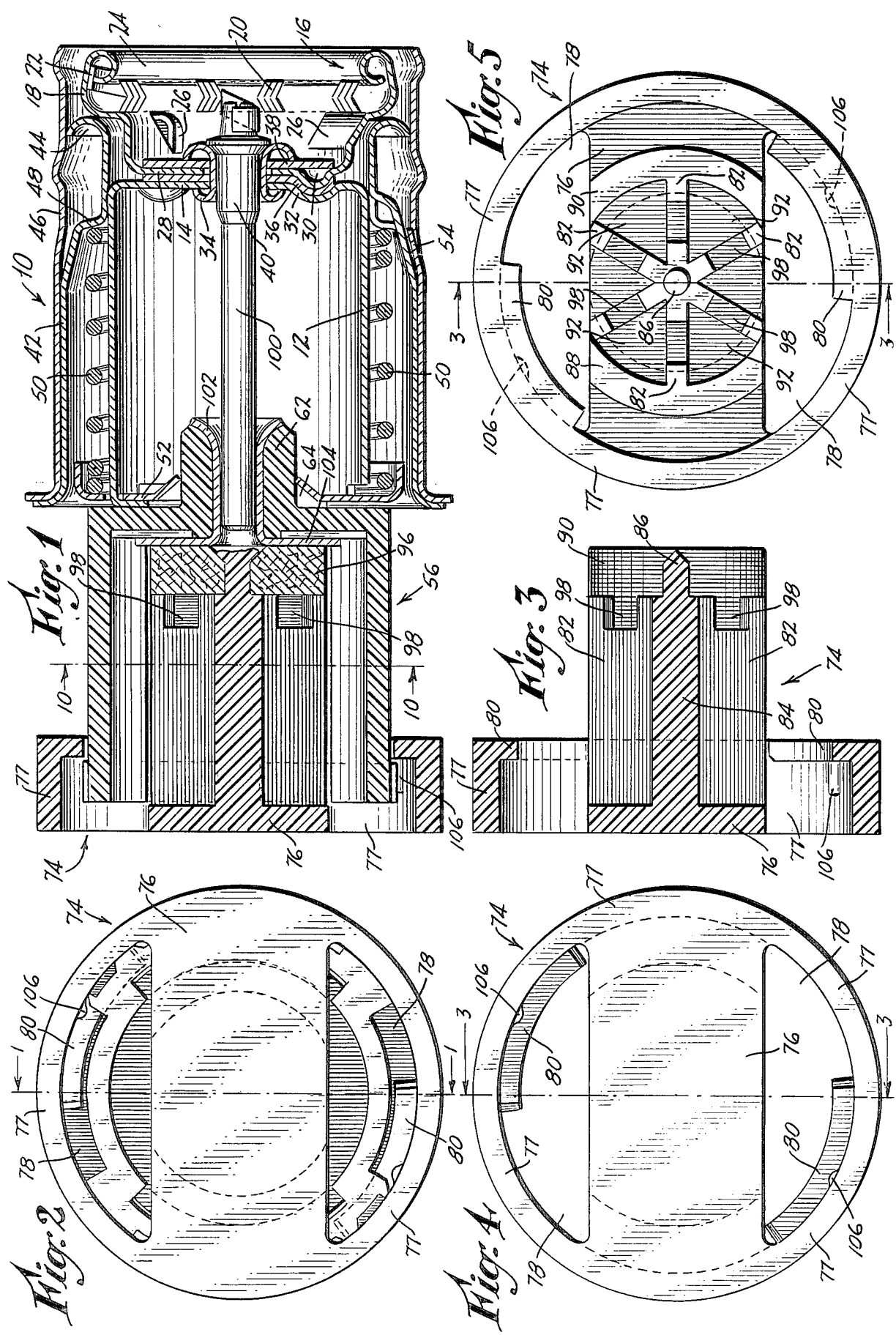

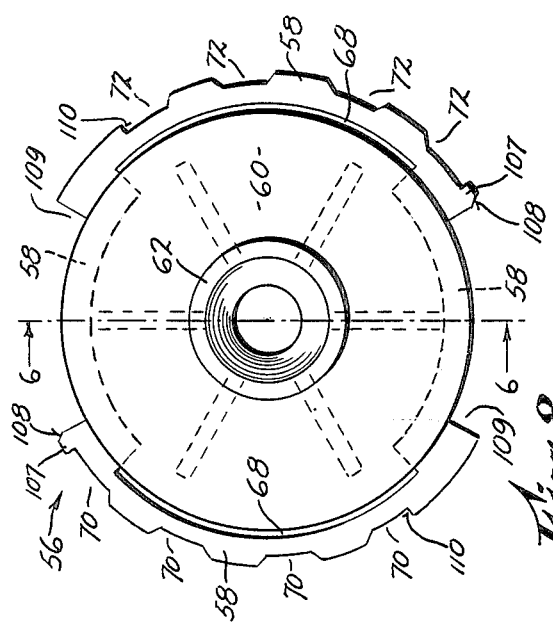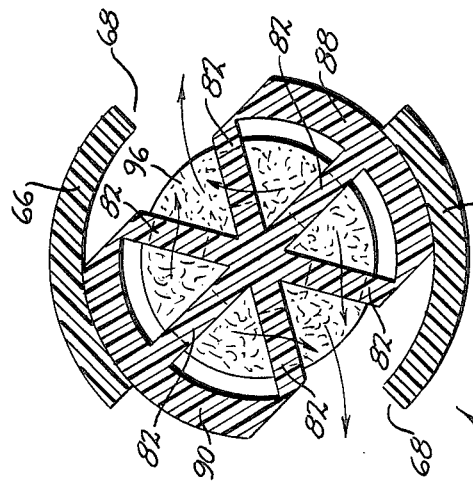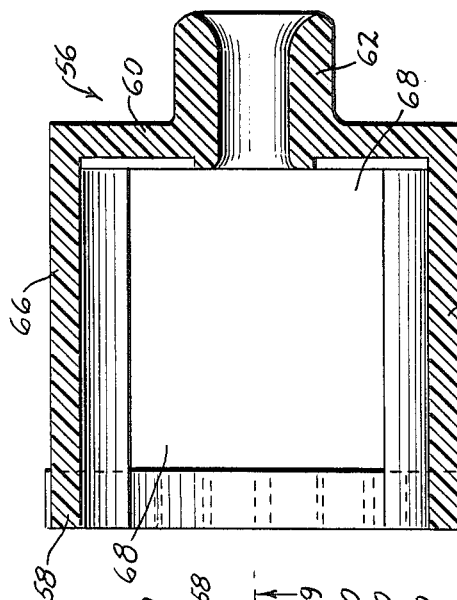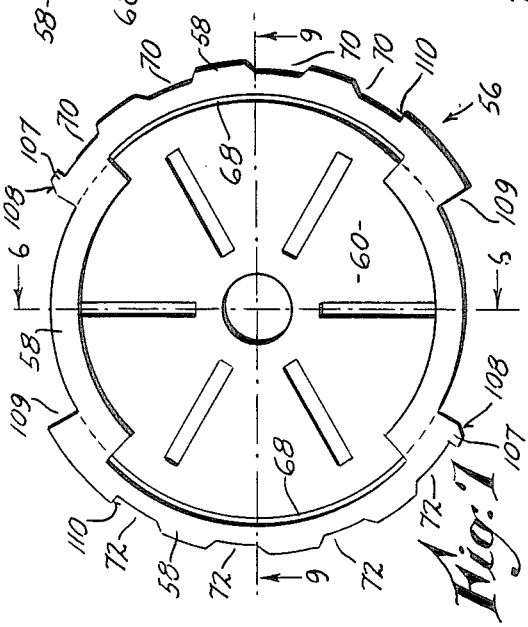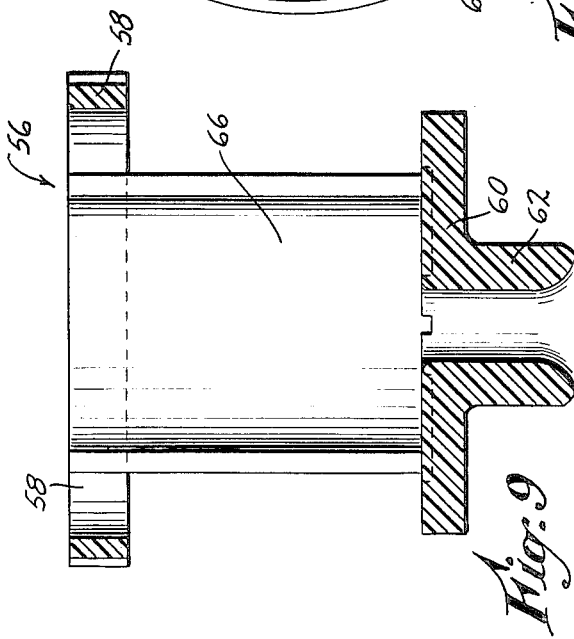

ELECTRIC CIGAR LIGHTER HAVING AROMATIC EMITTING MEANS

STATEMENT AS TO RIGHTS TO INVENTIONS MADE UNDER FEDERALLY SPONSORED RESEARCH AND DEVELOPMENT.

Research and development of the present invention and application have not been Federally-sponsored, and no rights are given under any Federal program.

BACKGROUND OF THE INVENTION

FIELD OF THE INVENTION

This invention relates generally to automotive electric cigar lighters of the type containing aromatic substances which respond to heat produced by the igniting coil of the lighter and emit various pleasing fragrances or aromas into the passenger compartment of a vehicle.

DESCRIPTION OF THE RELATED ART INCLUDING INFORMATION DISCLOSED UNDER 37 CFR §§1.97-1.99

A typical scent-producing cigar lighter is illustrated and described in U.S. Pat. No. 4,574,181 issued Mar. 4, 1986 to D Spector, and entitled AROMA-GENERATING AUTOMOBILE CIGARETTE LIGHTER.

This patented device incorporates an ignitor plug having a conventional spiral wound heating element disposed at its inner end, and having a tubular body adapted to be received in a socket or well containing suitable bimetal contacts for engagement with the heating element cup of the plug, to effect energization of the element. The body contains an insulating support member in which there is slidably received a cartridge containing an aromatic substance that responds to the heat of the igniting coil and releases a fragrance into the automobile interior. Each time the lighter is activated, a small amount of aromatic vapor is released. The cartridge can be replaced from the front of the lighter plug, through the knob thereof. A replacement cartridge of similar or different aroma can then be substituted.

One of the problems with this design is that the aromacontaining substance is in the form of a cartridge having a core carried in a ceramic tube which is positioned deep in the interior of the ignitor plug, adjacent to the heating element. Reliance is placed on the ability of the vapor that is emitted to flow between the walls of the ceramic tube and the cartridge, in order to arrive at the front of the unit. Since air circulation in this constricted space is usually inadequate, only a small fraction of the vapors arrive at the desired area, in front of the lighter. Moreover, the exposed surface area of the fragrancecontaining material is limited. The inner portions of the fragrant core are mostly confined, and thus not subjected to as much heat as is the end surface of the core. As a consequence, the overall efficiency is poor and the release of vapors tends to be sporadic.

Furthermore, the patented device deviates considerably in its structure from that of a typical, modern automotive ignitor plug such as that illustrated in U.S. Pat. No. 3,870,857. In particular, the '181 patent does not reveal the details of the electrical connections of the heating coil and the ignitor plug; also, the nature of the electrical connection to and mechanical support of the center of the coil is not made clear. It appears that special structures are required, as for example with regard to the apertured plunger and associated knob. It is also not apparent that the device illustrated can be fabricated in the exact form shown and still result in an operative and rugged unit that is capable of long, reliable service over multiple cycles of operation and extended periods of time.

SUMMARY OF THE INVENTION

The above disadvantages and drawbacks of prior scent-emitting cigar lighters are obviated by the present invention, which has for one object the provision of a novel and improved scent-producing lighter which is both extremely simple in construction and reliable in operation.

Another object of the invention is to provide an improved scent-producing lighter in accordance with the foregoing, wherein increased release of fragrant vapors is realizeable as a consequence of improved air circulation in the vicinity of the material containing the scented substance.

A related object of the invention is to provide an improved scent-producing lighter as above set forth, which is largely adaptable to the structure of existing ignitor plugs whereby many of the structural components of such plugs can be incorporated directly in the lighter design, with a minimum of manufacturing changes that would necessitate re-tooling and the attendant expense involved therewith.

Still another object of the invention is to provide an improved scent-producing lighter as above characterized, wherein the manufacturing cost is maintained as low as possible, largely through the use of molded parts and metal components having a simple configuration.

Yet another object of the invention is to provide an improved scent-producing lighter of the kind indicated, wherein replacement or substitution of the scent-emitting substance is readily accomplished from the front of the lighter, and with a simple twist-and-retract movement of a replaceable cartridge, that is readily understandable by the user.

A still further object of the invention is to provide an improved scent-producing lighter as outlined above, wherein the extent of emission of the scent-containing substance to the vehicle interior can be adjusted by the user, so as to permit increases or decreases in the amount of scented vapor that is emitted with each subsequent energization of the lighter.

A further object of the invention is to provide an improved scent-producing lighter in accordance with the foregoing, where in adjustment in the rate of venting of the scent-emitting substance is capable of calibration by virtue of cooperable detent structures on the knob and on the cartridge containing the active substance.

The above objects are accomplished by a scent-emitting electric cigar lighter comprising an igniting unit having a plug body with an electric heating element at its inner end, a metal conductor stud connected to the heating element in heat-exchanging relation therewith and extending forwardly through the plug body, and a heat transfer flange at the forward end of the stud. A slab of fragrant substance is disposed adjacent the heat-transfer flange in heat-exchanging relation therewith. At the front of the body there is a knob which surrounds the fragrant slab.

Preferably the fragrant substance is carried on a removable cartridge which can be inserted into and removed from the knob from the front of the lighter. Upon initial insertion, the cartridge can be turned with respect to the knob such that the cartridge will be held captive on the knob until the user decides to remove it, as when it is desired to substitute a fresh cartridge containing a new supply of scented substance of either the same fragrance or a different fragrance.

Other features and advantages will hereinafter appear.

BRIEF DESCRIPTION OF THE DRAWINGS

In the drawings, illustrating a preferred embodiment of the invention:

FIG. 1 is an axial sectional view of the improved scent-producing lighter of the present invention, illustrating details of the ignitor plug structure, and of the knob and cartridge assembly carried by the front of the ignitor plug. The section is taken on the line 1—1 of FIG. 2.

FIG. 2 is a left end elevation of the scent-producing lighter of FIG. 1.

FIG 3 is an axial sectional view of the removable cartridge carried by the knob of the lighter. The section is taken on the line 3—3 of FIG. 4, and the line 3—3 of FIG. 5.

FIG. 4 is a left end elevation of the cartridge of FIG. 3.

FIG. 5 is a right end elevation of the cartridge of FIGS. 3 and 4.

FIG. 6 is an axial section of the knob of the scent-producing lighter of FIG. 1, which is permanently installed on and retained by the front of the ignitor plug as in FIG. 1. The section is taken on the line 6—6 of FIG. 7, and the line 6—6 of FIG. 8.

FIG. 7 is a left end elevation of the knob of FIG. 6.

FIG. 8 is a right end elevation of the knob of FIGS. 6 and 7.

FIG. 9 is an axial section taken on the line 9—9 of FIG. 7.

FIG. 10 is a transverse section taken on the line 10—10 of FIG. 1.

FIG. 11 is a fragmentary section similar to FIG. 10, showing the cartridge of the lighter turned in a clockwise direction with respect to the knob, so as to increase the size of vent passages defined by the knob and cartridge and thereby increase the rate of release of aromatic vapors contained in the vaporemitting substance.

DESCRIPTION OF THE PREFERRED EMBODIMENT

Figure 13:
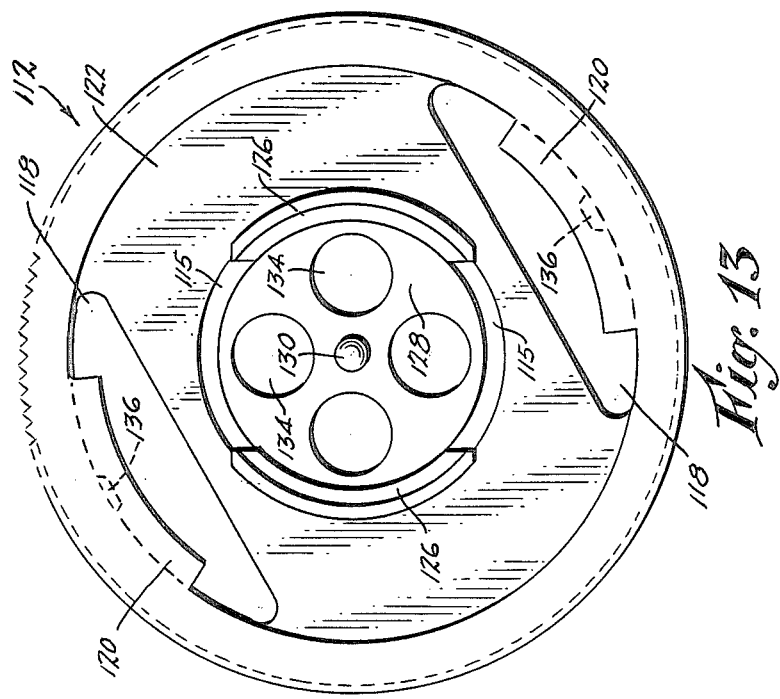
FIG. 13 is a right end elevation of the cartridge of FIG. 12.

Referring first to FIG. 1 there is illustrated a cigar lighter ignitor plug generally designated by the numeral 10, which is adapted for insertion in a cooperable socket or well, such as that illustrated in U.S. Pat. No. 3,870,857 identified above. Since the structure of the socket forms no part of the present invention, discussion will be limited to the construction of the ignitor plug and its associated scent-producing components.

The ignitor plug comprises a tubular body 12 having a transverse end wall 14. Attached to the wall 14 is a contact or heating element cup 16 having a shouldered side wall 18 which is grasped by bimetallic spring fingers (not shown) in the cigar lighter well when the ignitor plug 10 is depressed, in the conventional manner.

The heating element cup 16 carries a spiral wound igniting coil 20 having an outer convolution 22 laterally offset with respect to the plane of the coil. This convolution is preferably mechanically and electrically engaged by a curled rim 24 of the cup, such that good electrical contact is established therewith. Mechanical support of this outer convolution 22 is also provided.

The cup 16 has a series of inwardly lanced support shoulder or lugs 26 which back up the coil 20, typically at six circumferentially-spaced locations, and provide mechanical support. Two such lugs 26 are illustrated in FIG. 1.

The cup 16 has a transverse bottom wall 28 with one or more projecting nibs 30 that are intended to cooperate with a series of concavities 32 on the transverse wall 14 of the tubular body 12. An eyelet 34 mechanically secures the heating element cup 16 to the tubular body 12. An insulating washer 36 of mica or other suitable substance is interposed between the transverse walls 14, 28, and in addition a second insulating washer 38 is located between the eyelet 34 and transverse wall 28 of the contact cup 16. The arrangement is such that the contact cup 16 remains electrically insulated from the tubular body 12 and eyelet 34.

In FIG. 1 of the drawings, one nib 30 is shown as occupying one concavity 32. The mica washer 36 is deformed when the eyelet 34 is installed; at the same time, a desired self-seeking positioning of the contact cup 16 with respect to the body 12 is obtained, as a result of a tendency for each nib 30 to become seated in one of the concavities 32. Typically three nibs 30 are employed, with nine concavities 32 on the transverse wall 14 of the body 12.

Pressed into the eyelet 34 is a slotted rivet 40; the inner end of the heating coil 20 is received in the slot of the rivet and crimped in position therein. By such arrangement, the inner end or convolution is electrically connected to the rivet 40 and tubular body 12, whereas the outer convolution is electrically at the potential of the contact cup 16, which receives 12 volts d. c. from the bimetallic fingers (not shown), when the ignitor plug 10 is depressed in its socket.

Slidably carried on the tubular body 12 is a friction sleeve 42 having at its inner end an annular outward curl 44 that bears against the inner surface of an ashguard 46, to be described below. The sleeve 42 also has an annular shoulder 48 constituting a seat for one end of a compression spring 50. The other end of the spring 50 is seated against a cap member 52 that is secured to the outer end of the tubular body 12 by suitable tabs (one being shown in FIG. 1, but having no identifying number) which are received in slots in the cap member 52 and thereafter bent over. The compression spring 50 biases the friction sleeve 42 to a position wherein the annular curl 44 thereof engages the contact cup 16, as in FIG. 1, when the ignitor plug is not being energized.

The ashguard 46 is telescopically carried on the friction sleeve 42. When the ignitor plug is withdrawn from the cigar lighter socket, one or more radially inwardly projecting teeth 54 in the ashguard 46 are engaged by the curl 44 of the friction sleeve 42, to limit the degree of movement between the two parts. The ashguard 46 can thus move between the position of FIG. 1 with respect to the friction sleeve 42, and a position wherein the sleeve 42 and contact cup 16 are retracted in the ashguard an extent, and the tooth 54 shown in FIG. 1 is engaged by the curl 44. The tooth 54 and curl 44 thus constitute a positive stop to prevent further retraction of the ashguard 46 past a predetermined, desired position.

In accordance with the present invention there is provided, in combination with the ignitor plug structure 10 described above, a novel and improved captive knob and removeable cartridge assembly containing a quantity of scented, vapor-emitting material that responds to heat generated by the heating coil when the ignitor plug is depressed and the coil energized. The vapor emitting material can be constituted of cotton fibers, felt, or open cell foam plastic that has been impregnated with volatile oil or liquid having the desired fragrance.

The knob 56 is particularly illustrated in FIGS. 6-9, and has a front annular peripheral rim portion 58, and a rear transverse apertured wall 60. A tubular boss 62 extends rearwardly from the transverse wall 60, and is adapted to be received and held permanently captive in a central hole or locking recess 64 of the cap 52 of the ignitor plug, as in FIG. 1. The recess 64 is formed by a series of radially inwardly extending, rearwardly-bent lugs having sharp edges. The boss 62 is press-fitted into the recess 64, and the sharp edges bite into the relatively softer outer surface of the boss 62 in the manner of a push-on or speed nut. The knob 56 is thus permanently retained on the plug 10 in the position of FIG. 1.

Extending between the front rim 58 and transverse rear wall 60 of the knob 56 are two oppositely disposed arcuate or curvilinear wall segments 66, shown in FIGS. 6, 9, 10 and 11, each extending through an arc of roughly 90 degrees. There exist oppositely disposed spaces or windows 68 between the adjacent edges of these wall sectors. The spaces constitute, together with cooperable arcuate wall sections of a cartridge to be described below, vent passages that can be selectively opened or closed.

As shown in FIG. 7, the outer surface of the rim 58 has a plurality of detent notches 70, 72, shown as two pairs of four notches each, which cooperate respectively with two detent nibs on the cartridge to be described, and which function to resist free turning between the cartridge and knob. The rim also has stop shoulders which cooperate with the detent nibs to limit relative turning movement between the cartridge and knob to approximately 90 degrees.

The cartridge 74 is particularly illustrated in FIGS. 3-5. It comprises a one-piece molded plastic part having a front wall 76 including an annular front rim 77 and containing two arcuate slots 78, FIG. 4, and two oppositely-disposed arcuate shoulders or retainer sectors 80 spaced axially from the top wall. The sectors 80 each extend through an arc of approximately 60 degrees. After installation, portions of the knob rim 58 are received between this top wall 76 and the arcuate sectors 80 such that the cartridge 74 will be retained thereon.

The cartridge 74 has a fluted body portion. Extending rearwardly from the front wall 76 of the cartridge is a series of six radially extending spokes 82, and a central stem 84. The end of the stem 84 has a tapered portion 86. In addition, a first arcuate wall section 88 connects the edges of three of the spokes 82, and a second, similar arcuate wall section 90 connects the edges of the remaining three spokes 82.

Two chambers 92 are formed by each arcuate wall section 88, 90 and its adjoining three spokes 82. Also, two open V-shaped troughs 94, FIG. 10, are similarly formed. In an axial direction, both of these arcuate wall sections 88, 90 extend inwardly beyond the six spokes 82, and form semi-cylindrical boundaries adapted to receive and confine an apertured slab 96 of scent-releasing material, shown in FIG. 1. The spokes comprise walls of generally planar configuration, and each wall has a notch 98 at its bottom end, the notches 98 providing communication between the four chambers 92 that are formed between the spokes 82, FIGS. 10 and 11, and the two open V-shaped troughs 94.

By the present invention, the arcuate wall sections 88, 90 constitute shutters on the cartridge 74, which together with the curvilinear wall segments 66 of the knob 56, can open or closeoff vent passages through which vapors from the slab 96 of scent-releasing material pass, according to the relative rotary position of the cartridge 74 with respect to the knob 56.

The tapered portion 86 of the stem 84 is received in a central aperture in the slab 96 of scent-releasing material. The portion 86 can have its end mushroomed, as in FIG. 1, to retain the slab 96.

Further in accordance with the invention, the rivet 40 has a thermally conductive forward extension 100 that projects forwardly to the area of the boss 62 of the knob 56, and is fitted into an eyelet 102 therein, the eyelet 102 having a generally circular heat-transfer flange 104 that snugly engages the slab 96 broadside, and thus is in good heat-exchanging relation therewith. The extension 100 can take the form of a sleeve that is pressed over the end of the rivet 40 or otherwise secured thereto; alternately it can be an integral part of the rivet 40, having a reduced diameter as shown. The eyelet 102 is pressed into the knob 56 and flared over, as shown in FIG. 1; in addition there exists a press fit between the extension 100 on the rivet 40 and the walls of the eyelet 102 in the boss 62. The arrangement is such that heat from the coil 20 is transferred through the rivet extension 100 to the eyelet 102, and thereafter to the slab 96, causing the latter to release a quantity of fragrant vapor to the four chambers 92 and two V-shaped troughs 94 formed by the spokes 82 of the cartridge.

Exchange of vapor between the chambers and troughs occurs by virtue of the notches 98 that are provided in the lower ends of the spokes 82, FIGS. 1, 3 and 5.

Referring again to FIGS. 2, 4 and 7, there are oppositely disposed detent nibs 106 projecting radially inwardly from the surfaces of the slots 78 into the path of movement of shoulders 107 having camming surfaces 108, the shoulders 107 defining the first set of notches 70, 72 of the knob in FIG. 7. During initial assembly of a fresh cartridge 74 onto an existing knob 56, the cartridge 74 is aligned circumferentially such that the retainer sectors 80 can be passed axially inwardly through arcuate spaces 109 in the periphery of the knob 56, FIG. 7, until the slab 96 engages the heat-transfer flange 104 of the eyelet 102, FIG. 1. Thereafter, the cartridge 74 is turned clockwise with respect to the stationary knob 56 (and ignitor plug 10) until the nibs 106 arrive at the camming surfaces 108, FIG. 7. The parts will now have the relative positions shown in FIG. 2. The engagement of the retainer sectors 80 with the underside of the knob periphery 58 maintains pressure between the slab 96 and the eyelet flange 104.

Due to the yieldability of the plastic substances of which the cartridge 74 and knob 56 are constituted, as the cartridge 74 is forced clockwise in FIG. 2, the nibs 106 can by-pass the camming surfaces 108 of the shoulders 107, corresponding to relative positions just beyond that shown in FIG. 2, with the nibs 106 ultimately arriving at the first pair of notches 70, 72 respectively. In this position, the arcuate wall sections 88, 90 of the cartridge 74 do not overlap the arcuate wall sections 66 of the knob 56, and thus the knob and cartridge have the relative positions shown in FIG. 10. Under these conditions the slab 96 of fragrant material is not vented, and vapors therefrom are confined mostly to the four chambers 92 formed by the spokes 82 of the cartridge 74, and the area inside the arcuate walls 66 of the knob.

Rotation of the cartridge 74 in a clockwise direction in FIG. 2 causes the nibs 106 to arrive at the second, adjacent pair of notches 70, 72 respectively, FIG. 7, in the knob periphery, resulting in partial overlap of the wall sections 66 of the knob and wall sections 88, 90 of the cartridge. Limited venting of vapors emitted by the slab of fragrant material occurs, as in FIG. 11, as shown by the arrows. The chambers 92 vent through the notches 98 to the V-troughs 94, and the latter in turn vent forwardly through the arcuate slots 78 in the top wall 76 of the cartridge 74, as can be readily understood. Third and fourth notch pairs 70, 72 are provided, and as the cartridge is turned further, increased venting will occur due to the decreased overlap of the wall sectors 66 with the shutters or wall segments 88, 90 respectively. A fully vented condition would correspond to the arrival of the nibs at the fourth pair of notches 70, 72. The shoulders 110 at the ends of this pair are sharp and thus prevent the cartridge 74 from being turned further clockwise wherein the nibs 106 would by-pass them.

Replacement of a depleted cartridge 74 is accomplished by initially turning the cartridge in a counter-clockwise direction, causing the nibs 106 to forcibly by-pass the shoulders 107 at the first notch pair 70, 72, permitting alignment of the retainer sectors 80 with the arcuate clearance spaces 109 in the knob. Thereafter the cartridge 74 can be removed axially from the knob 56, i.e. to the left in FIG. 1.

Another embodiment of the invention is illustrated in FIGS. 12–15, showing a modified cartridge 112 of a design similar to that of the previous embodiment, but somewhat simplified. The cartridge 112 comprises a one-piece molded plastic part having a front wall 114 including an annular front rim 116 and containing an opening 115, two arcuate slots 118, and two oppositely-disposed arcuate shoulders or retainer sectors 120 spaced axially from the front wall 114. The sectors 120 each extend through an arc of approximately 60 degrees. After installation, portions of the knob rim 58 are received between this front wall 114 and the arcuate sectors 120 such that the cartridge 112 will be retained thereon.

Figure 14:
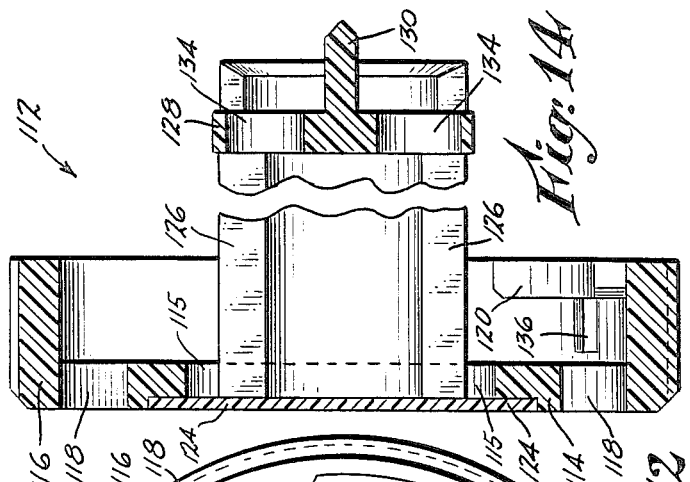
FIG. 14 is an axial sectional view of the cartridge of FIGS. 12 and 13, taken on the line 14—14 of FIG. 12.
Figure 12:
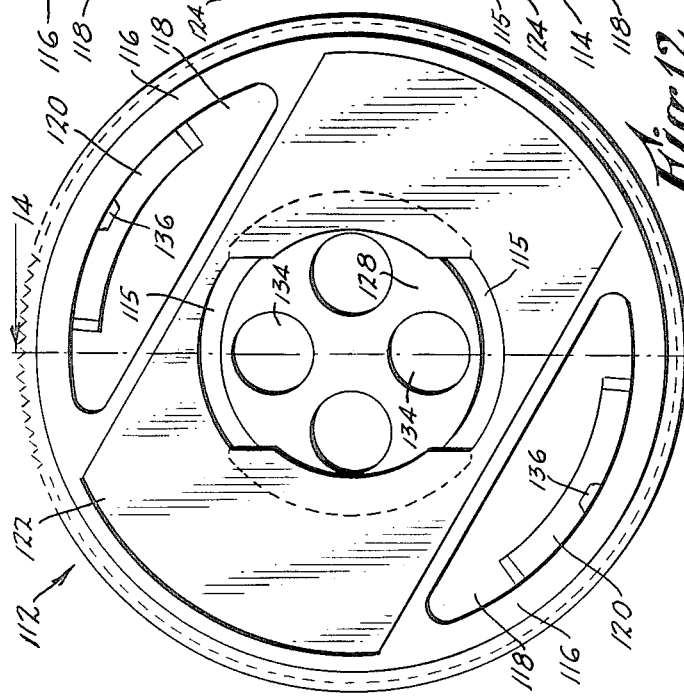
FIG. 12 is a left end elevation of a modified cartridge intended to be substituted for the cartridge shown in FIGS. 3-5, constituting another embodiment of the invention.
Figure 15:
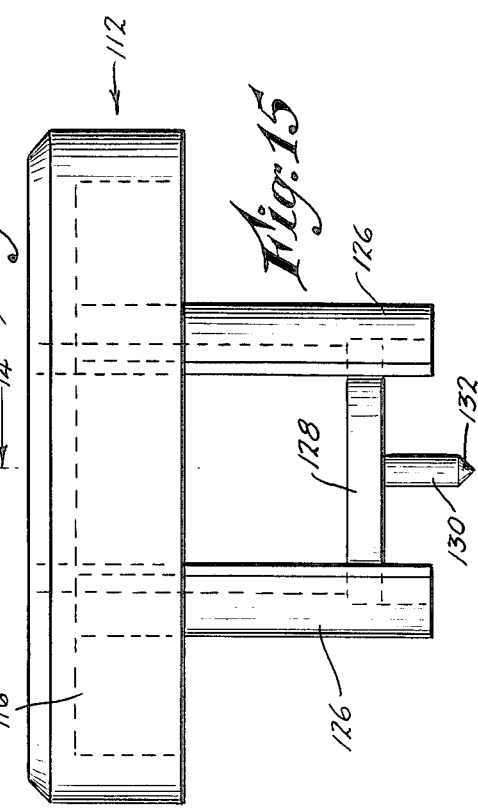
FIG. 15 is a front elevation of the cartridge of FIGS. 12-14.

In the outer surface of the front wall 114 is a shallow recess 122 for receiving as an insert, a cover plate, nameplate or other type of applique 124, FIG. 14, preferably constituted of aluminum or plastic. This component can be cemented in place following molding of the body of the cartridge 112.

The cartridge 112 has oppositely disposed rearwardly extending arcuate wall sections 126, and a transverse, apertured rear wall 128 carrying a central stem 130. The end of the stem has a tapered portion 132.

The rear surface of the wall provides a seat against which a slab 96 (FIG. 1) of scent-releasing material is secured. During assembly, the stem 130 is passed through a hole in the slab 96, as in the previous embodiment, and can be mushroomed as in FIG. 1, to retain the slab. When the cartridge is installed in the knob 56, the slab is sandwiched between the wall 128 and the flange 104. Scent from the slab 96 passes forwardly through apertures 134 in the wall 128, to the area between the two arcuate wall segments 126.

By the invention, the arcuate wall segments 126 constitute shutters on the cartridge 112 which together with the curvilinear wall segments 66 of the knob 56, can open or close-off vent passages comprising slots 118 through which vapors from the slab 96 of scent-releasing material pass, according to the rotary position of the cartridge 112 with respect to the knob 56.

As in the previous embodiment, on the cartridge 112 there are oppositely disposed detent nibs 136 projecting radially inwardly from the surfaces of the slots 118 into the path of movement of the shoulders 107 (FIG. 7) having the camming surfaces 108, the shoulders 107 partially defining the first set of notches 70, 72 of the knob in this figure. Assembly is accomplished in the same manner as described above. In particular, the cartridge 112 is aligned circumferentially such that the retainer sectors 120 can be passed axially inwardly through arcuate spaces 109 in the periphery of the knob 56, FIG. 7, until the scent-emitting slab 96 engages the heat-transfer flange 104 of the eyelet 102, FIG. 1. Thereafter, the cartridge 112 is turned clockwise with respect to the stationary knob 56 (and ignitor plug 10) until the nibs 136 arrive at and by-pass the camming surfaces 108, to occupy the first set of notches 70 and 72, FIG. 7. The arrangement is such that with the nibs occupying these notches, venting of scented vapor through the arcuate slots 118 is prevented, since the arcuate wall segments 126 and wall segments 66 of the knob 56 are in positions similar to the showing of FIG. 10, wherein they form a closed chamber. "Dialing" or rotating the cartridge 112 clockwise, such that the nibs 136 occupy successive pairs 70, 72 of notches results in overlapping of the segments 66 with the corresponding wall segments 126 of the cartridge 112. A fully venting condition would prevail when the nibs 136 arrive at the notch pairs 70, 72 adjacent the shoulders 110 of FIG. 7. As before, upon use of the lighter, heat conducted through the eyelet 102 causes release of scented vapors from the slab 96, such vapors travelling forwardly through the arcuate slots 118 shown in FIGS. 12 and 13, and out into the passenger compartment of the vehicle.

In other respects the operation of the cartridge 112 of FIGS. 12–15 in connection with the knob 56 is similar to that already described above in connection with the cartridge 74 of FIGS. 3–5 and knob 56.

The disclosed construction has the following significant advantages. Assembly is readily accomplished, since the knob 56 is merely forcibly inserted into the cap 52 of the ignitor plug 10 at the same time that the eyelet 102 is pressed over the rivet extension 100. Thereafter, the knob 56 is permanently retained in this position.

In the case of the first embodiment, installation and replacement of the cartridge 74 is also facilitated, since all that is required is a two-step operation involving axial insertion of the cartridge 74 onto the knob 56, followed by a turning of the cartridge 74 in a clockwise direction. Various degrees of exposure of the slab 96 of fragrant material are possible by merely "dialing" the desired vent opening (defined by shutters 66 and segments 88, 90 in FIGS. 10 and 11) corresponding to seating of the detent nibs 106 in one of four pairs of notches 70, 72 in the periphery of the rim of the knob. The release of scent can thus be calibrated or pre-set, to suit the particular conditions of use. In addition, as the fragrant oil or liquid contained in the slab gradually becomes depleted, the cartridge can be turned clockwise to the next position corresponding to a larger vent opening so as to compensate for such depletion.

Both the knob 56 and cartridge 74 are preferably molded plastic components, each being a single unitary piece, thereby keeping the manufacturing expense as low as practical.

Interchangeability of cartridges is also possible, permitting the user to choose a variety of fragrances, and to substitute one for another, if desired.

Finally the disclosed device can be readily adapted for use with ignitor plugs of modern, automated design, and which have been found to be rugged and reliable over many thousands of cycles of operation. It can be readily appreciated that plugs of the type shown in U.S. Pat. No. 3,870,857 identified above incorporate many improvements which are the result of refinements made over a period of many years. Such improvements have been found to contribute greatly to long life and manufacturing economy.

With the present construction involving the fragrance-producing feature, there is encountered absolutely no interference with normal cigar lighter operation; if the user so desires, the fragrancing feature can be omitted by merely inserting a blank cartridge, that is, one containing no scent-releasing slab.

The disclosed devices are thus seen to represent a distinct advance and improvement in this field.

Variations and modifications are possible without departing from the spirit of the invention.

Each and every one of the appended claims defines an aspect of the invention which is separate and distinct from all others, and accordingly it is intended that each claim be treated in this manner when examined in the light of the prior art devices in any determination of novelty or validity.

What is claimed is:

1. A scent-emitting electric cigar lighter comprising, in combination:
   (a) an igniting unit having a plug body and having at one end of said body an electric heating element,
   (b) a metal conductor stud connected to said heating element in heat-exchanging relation therewith, said stud extending through said body and having a terminus terminating at the other end thereof,
   (c) a heat transfer flange attached to the terminus of said stud,
   (d) a slab of fragrant substance disposed adjacent said heattransfer flange in heat-exchanging relation therewith, and
   (e) a knob attached to the other end of the igniting unit body and surrounding said fragrant slab.

2. A scent-emitting electric cigar lighter as set forth in claim 1, and further including:
   (a) a cartridge detachably carried by said knob,
   (b) said fragrant slab being mounted on said cartridge.

3. A scent-emitting electric cigar lighter as set forth in claim 2, wherein:
   (a) said knob and cartridge are telescopically disposed one within the other.

4. A scent-emitting electric cigar lighter as set forth in claim 3, wherein:
   (a) the cartridge is disposed within the knob and has a rim portion disposed exteriorly of the knob.

5. A scent-emitting electric cigar lighter as set forth in claim 4, wherein:
   (a) said knob and cartridge have cooperable twist-lock means for holding them together.

6. A scent-emitting electric cigar lighter as set forth in claim 3, wherein:
   (a) said knob and cartridge have registerable passages for conducting vapors from said slab to the surrounding atmosphere,
   (b) relative rotary movement between the knob and cartridge enabling said passages to register with each other to a greater or lesser extent, thereby to provide for an adjustable porting of the vapors from the slab to the exterior.

7. A scent-emitting electric cigar lighter as set forth in claim 3, wherein:
   (a) said cartridge has a large frontal annular rim and a transverse wall connected with the rim, said wall and rim defining a pair of opposite recesses,
   (b) said knob having an annular edge portion disposed within said rim and behind said recesses.

8. A scent-emitting electric cigar lighter as set forth in claim 7, wherein:
   (a) the annular rim of the cartridge and the annular edge portion of the knob have cooperable yieldable detent means for holding the cartridge in any of a number of different rotative positions with respect to the knob.

9. A scent-emitting electric cigar lighter as set forth in claim 2, wherein:
   (a) the cartridge has a fluted body portion to which said slab is secured.

10. A scent-emitting electric cigar lighter as set forth in claim 9, wherein:
    (a) the flutes of the cartridge body portion have passages which connect the spaces between the flutes to each other.

11. A scent-emitting electric cigar lighter as set forth in claim 7, wherein:
    (a) the knob and cartridge have cooperable twist-lock means comprising an arcuate retainer sector on the annular rim of the cartridge and an arcuate retainer sector on the annular edge portion of the knob, said retainer sectors being cooperable to hold the cartridge captive on the knob.

12. A scent-emitting electric cigar lighter comprising, in combination:
    (a) an igniting unit having a plug body and having at one end of said body an electric heating element,
    (b) a knob part mounted to the front of the plug body,
    (c) a cartridge part containing fragrant substance,
    (d) means carried by said plug body, for transferring heat from said heating element to said fragrant substance when the heating element is energized, and
    (e) cooperable means on said knob and cartridge parts, providing a vent opening at the front of said igniting unit, for channelling aromatic vapors from said fragrant substance to the exterior of the cigar lighter.

13. The invention as set forth in claim 12, wherein:

(a) the size of the vent opening provided by the cooperable means is adjustable by movement of the knob and cartridge parts relative to one another.

14. The invention as set forth in claim 13, and further including:
   (a) means on said knob and cartridge parts, providing at least one detent in the path of movement of said parts, to indicate to the user the relative positions thereof, and hence the size of the vent opening.

15. The invention as set forth in claim 13, and further including:
   (a) means on said knob and cartridge parts, providing multiple detents in the path of movement of said parts, to indicate to the user the relative positions thereof, and hence the size of the vent opening.

16. The invention as set forth in claim 12, wherein:
   (a) said cooperable means comprises a front wall of the cartridge part, and means defining an aperture therein, and
   (b) arcuate walls on said cartridge part and said knob part, one of said walls being adapted for movement between an open position wherein it generally overlies the arcuate wall of the other part, and a closed position wherein it is disposed circumferentially spaced from the arcuate wall of the other part, to form an enclosure therewith.

17. A scent-emitting electric cigar lighter comprising, in combination:
   (a) an igniting unit having a plug body and having at one end of said body an electric heating element,
   (b) a knob part mounted to the front of the plug body,
   (c) a cartridge part containing scent-emitting substance,
   (d) cooperable retainer means on said knob and cartridge parts, for retaining the latter captive on the knob part in response to axial assembly of the cartridge part thereon and subsequent turning of the said cartridge part relative to the knob part, and
   (e) means including a metallic conductor member carried by said plug body, for transferring heat from said heating element to said scent-emitting substance, when the cartridge part is installed on the knob part and the heating element is energized.

18. The invention as set forth in claim 17, wherein:
   (a) said heat transferring means comprises an elongate metal member connected to the heating element and extending forwardly through the plug body to the scent-emitting substance.

19. The invention as set forth in claim 18, wherein:
   (a) said scent-emitting substance comprises a wafer-like slab, and
   (b) a disk-like heat transfer member carried by the elongate metal member and disposed generally broadside to and engaging said wafer-like slab of scent-emitting substance.

20. The invention as set forth in claim 17, wherein:
   (a) said heat transferring means comprises a rivet having a slot at one end and in which an end convolution of the heating element is crimped, and
   (b) a disk-like heat transfer member carried by the rivet and in thermal heat-exchanging relation therewith and with the scent-emitting substance.

21. The invention as set forth in claim 2, wherein:
   (a) said cartridge has an expansive front wall provided with a recess, and
   (b) a cover plate received in said recess.

22. The invention as set forth in claim 2, wherein:
   (a) said cartridge has a front wall and a rear wall,
   (b) said fragrant slab being disposed substantially flat against said rear wall, and held captive thereon.

23. The invention as set forth in claim 2, wherein:
   (a) said cartridge has a front wall and a rear wall,
   (b) said rear wall being apertured to permit vapors from said fragrant slab to pass therethrough, and toward the front wall of the cartridge.

24. The invention as set forth in claim 2, wherein:
   (a) said cartridge has a front wall and a rear wall,
   (b) said slab being sandwiched between said rear wall and said heat transfer flange when the cartridge is installed on the knob.

25. The invention as set forth in claim 21, wherein:
   (a) said front wall has a through opening in said recess, to simplify molding of the cartridge,
   (b) the cover plate concealing the opening when assembled to the front wall.

* * * * *